United States Patent
Brodrick

(10) Patent No.: US 10,744,346 B2
(45) Date of Patent: Aug. 18, 2020

(54) COMMUNICATION APPARATUS FOR RADIATION THERAPY DEVICE

(71) Applicant: Elekta Limited, West Sussex (GB)

(72) Inventor: James Edward Brodrick, West Sussex (GB)

(73) Assignee: Elekta Limited, Crawley (GB)

( * ) Notice: Subject to any disclaimer, the term of this patent is extended or adjusted under 35 U.S.C. 154(b) by 106 days.

(21) Appl. No.: 16/010,884

(22) Filed: Jun. 18, 2018

(65) Prior Publication Data
US 2018/0369613 A1 Dec. 27, 2018

(30) Foreign Application Priority Data
Jun. 23, 2017 (GB) .................................. 1710115.5

(51) Int. Cl.
*A61N 5/10* (2006.01)
*H01Q 3/04* (2006.01)
*H01Q 21/20* (2006.01)

(52) U.S. Cl.
CPC ............. *A61N 5/1081* (2013.01); *A61N 5/10* (2013.01); *A61N 5/1039* (2013.01); *A61N 5/1048* (2013.01); *H01Q 3/04* (2013.01); *H01Q 21/205* (2013.01); *A61N 5/1047* (2013.01); *A61N 2005/1074* (2013.01)

(58) Field of Classification Search
CPC ...... A61N 5/1081; A61N 5/10; A61N 5/1039; A61N 5/1048; A61N 5/1074; A61N 2005/1074; H01Q 3/04; H01Q 21/205
See application file for complete search history.

(56) References Cited

U.S. PATENT DOCUMENTS

| 2,680,223 A | * | 6/1954 | Hammett | ................. | H01Q 3/04 |
| | | | | | 318/627 |
| 2,686,284 A | * | 8/1954 | Rudolph | ................. | H01Q 3/04 |
| | | | | | 318/282 |
| 2,745,994 A | * | 5/1956 | Dicke | ..................... | H01Q 3/04 |
| | | | | | 318/652 |

(Continued)

FOREIGN PATENT DOCUMENTS

| DE | 102009049052 A1 | 4/2011 |
| WO | WO-03053246 A1 | 7/2003 |
| WO | WO-2007034357 A2 | 3/2007 |

OTHER PUBLICATIONS

"United Kingdom Application Serial No. 1710115.5 Search Report and Examination dated Dec. 20, 2017", (Dec. 20, 2017), 6 pgs.

*Primary Examiner* — Blake C Riddick
(74) *Attorney, Agent, or Firm* — Schwegman Lundberg & Woessner, P.A.

(57) ABSTRACT

An apparatus for communicating with a radiation therapy device comprises a first plurality of omnidirectional radio antennas 212, 214 mounted upon a rotor 202, and a second plurality of omnidirectional radio antennas 216, 218 positioned at respective fixed locations off the rotor. The first plurality of antennas 212, 214 may be substantially equally spaced around the axis of rotation of the rotor 202. The first plurality of antennas 212, 214 and the second plurality of antennas 216, 218 are positioned so as to allow line-of-sight radio communication between at least one of the first plurality of antennas and at least one of the second plurality of antennas at all angles of rotation of the rotor 202.

18 Claims, 3 Drawing Sheets

(56) References Cited

U.S. PATENT DOCUMENTS

| | | | | |
|---|---|---|---|---|
| 4,424,516 A | * | 1/1984 | Kruger | H01Q 3/04 333/261 |
| 5,577,026 A | * | 11/1996 | Gordon | H01Q 1/38 343/841 |
| 2006/0274853 A1 | * | 12/2006 | Schilling | A61B 6/56 375/295 |
| 2008/0272296 A1 | * | 11/2008 | Frach | A61B 6/56 250/306 |
| 2009/0036780 A1 | * | 2/2009 | Abraham | A61B 8/08 600/459 |
| 2009/0105597 A1 | * | 4/2009 | Abraham | A61B 8/08 600/466 |
| 2010/0174189 A1 | * | 7/2010 | Abraham | A61B 5/076 600/439 |
| 2010/0177000 A1 | * | 7/2010 | Brisebois | H01Q 1/1257 343/703 |
| 2013/0225974 A1 | * | 8/2013 | Van Den Brink | A61N 5/1081 600/411 |
| 2013/0225975 A1 | * | 8/2013 | Harvey | A61B 5/0037 600/411 |
| 2013/0261430 A1 | * | 10/2013 | Uhlemann | A61N 5/1067 600/411 |
| 2013/0279647 A1 | * | 10/2013 | Krupica | G01N 23/046 378/19 |
| 2014/0003582 A1 | * | 1/2014 | Poulo | A61B 6/032 378/91 |
| 2015/0224341 A1 | * | 8/2015 | Vahala | G01R 33/4808 600/411 |
| 2016/0077175 A1 | | 3/2016 | Mori | |
| 2016/0256129 A1 | | 9/2016 | Ergler et al. | |
| 2016/0256712 A1 | * | 9/2016 | Vahala | A61N 5/1038 |
| 2017/0181723 A1 | * | 6/2017 | Abraham | A61B 6/56 |
| 2017/0251994 A1 | * | 9/2017 | Shippen | H01F 38/18 |
| 2018/0133518 A1 | * | 5/2018 | Harper | A61N 5/1045 |

* cited by examiner

US 10,744,346 B2

COMMUNICATION APPARATUS FOR RADIATION THERAPY DEVICE

CLAIM FOR PRIORITY

This application claims the benefit of priority of United Kingdom Application No. 1710115.5, filed Jun. 23, 2017, which is hereby incorporated by reference in its entirety.

TECHNICAL FIELD

The present disclosure generally relates to apparatuses for radiation therapy. Examples of the disclosure include, without limitation, apparatuses for radio communication with the rotor of a radiation therapy device.

BACKGROUND

Radiation therapy is a technique for killing cancerous cells with ionising radiation. Radiation therapy systems typically comprise a rotor with a source of ionising radiation, such as a linear accelerator, mounted thereon. Rotation of the rotor about a patient moves the linear accelerator, allowing radiation from the linear accelerator to be directed towards the patient from multiple directions.

Given the complexity of radiation therapy systems and the requirement for safety concerning the patient, it is imperative to provide real-time control of the system, especially of the rotor and the components mounted thereon. Prior radiation therapy systems have provided cables between the rotor and an off-rotor control unit to allow communication of control signals and data between the two. However, as the rotor rotates during therapy, the cables may wind about the rotor. Therefore, time must be taken between treatment sessions to rotate the rotor in the opposite direction to unwind the cables.

There is a need for real-time data communication with the rotor of radiation therapy devices that does not limit rotation of the rotor.

SUMMARY

Disclosed herein is an apparatus for radio communication with the rotor of a radiation therapy device. Particular examples of the disclosure enable real-time radio communication with the rotor without limiting rotor rotation.

In accordance with a first aspect, a communication apparatus for a radiation therapy device is provided, the radiation therapy device comprising a rotor that is rotatable about an axis of rotation to a plurality of angles of rotation. The apparatus comprises a first plurality of omnidirectional radio antennas positioned on the rotor. The apparatus further comprises a second plurality of omnidirectional radio antennas configured to communicate with the first plurality of antennas. Each of the second plurality of antennas is positioned at a respective fixed location off the rotor so as to allow line-of-sight radio communication between at least one of the first plurality of antennas and at least one of the second plurality of antennas at all angles of rotation of the rotor.

In accordance with a second aspect, a radiation therapy system is provided, the radiation therapy system comprising a rotor that is rotatable about an axis of rotation to a plurality of angles of rotation. The system further comprises a first plurality of omnidirectional radio antennas positioned on the rotor, and a second plurality of omnidirectional radio antennas configured to communicate with the first plurality of antennas. Each of the second plurality of antennas is positioned at a respective fixed location off the rotor so as to allow line-of-sight radio communication between at least one of the first plurality of antennas and at least one of the second plurality of antennas at each angle of rotation.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

Embodiments will now be described, purely by way of example, with reference to the accompanying drawings, wherein like elements are indicated using like reference signs, and in which.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open-ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Figure 1:
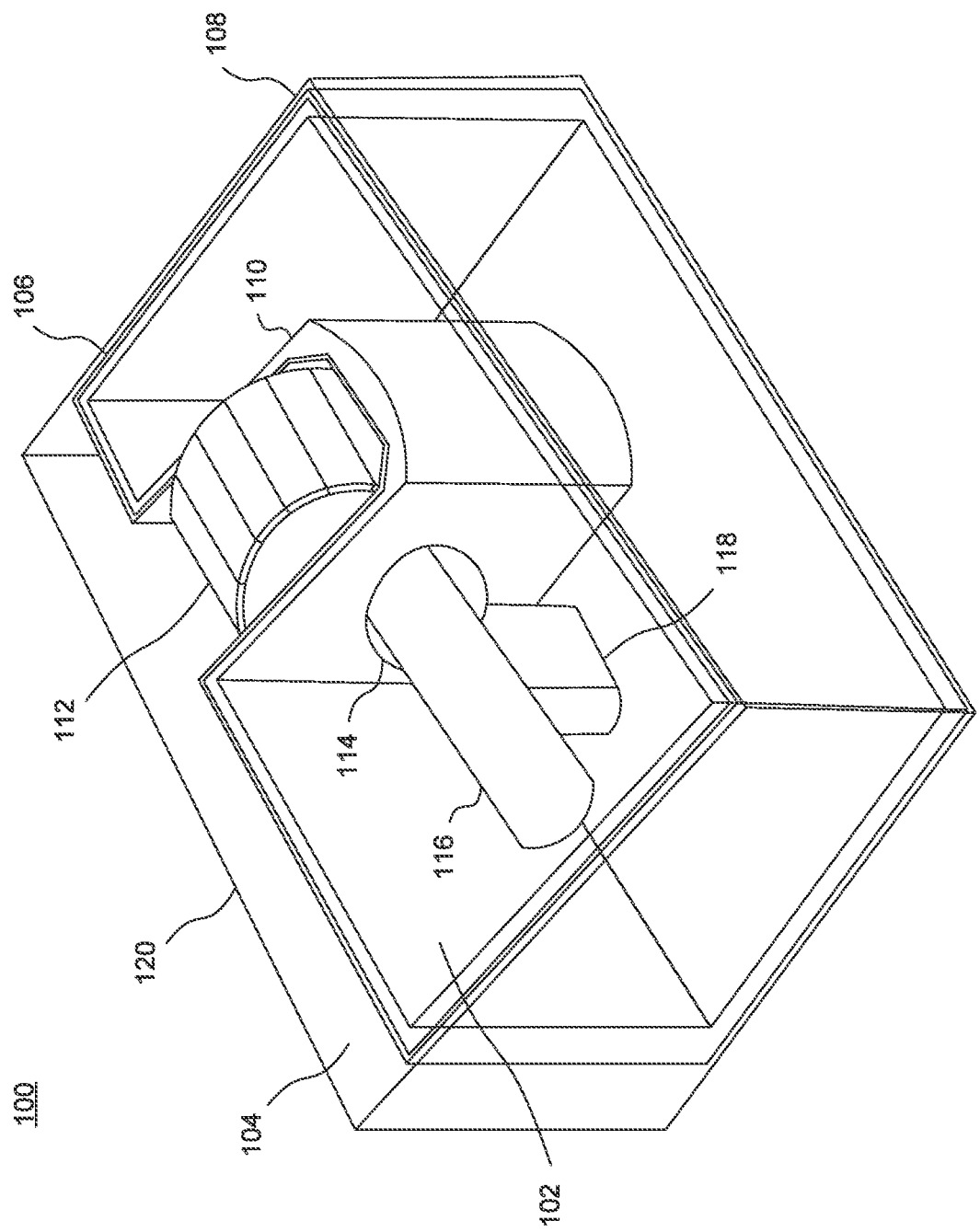
FIG. 1 illustrates a view of an exemplary radiation therapy system.

FIG. 1 illustrates a view of an exemplary radiation therapy system. System 100 may include radiation therapy device 112. Device 112 may be a linear accelerator (LINAC). Alternatively, device 112 may be a combination magnetic resonance imaging (MRI) device and linear accelerator, known as an MR-LINAC. However, it will be appreciated that device 112 in the present disclosure is not limited to a LINAC or MR-LINAC, and that the apparatuses disclosed herein may be used to enable any suitable radiation therapy device or any suitable combination medical imaging and radiation therapy device.

System 100 may include a treatment room 102 and a machine room 104. Treatment room 102 is formed by treatment room wall 108. In some embodiments, treatment room 102 may be rectangular except for an inward-facing extension of treatment room wall 108 which forms housing 110. Treatment room wall 108 is at least partially enclosed by shield 106. Shield 106 is provided to block external electromagnetic fields from interfering with components of system 100, such as radiation therapy device 112. For example, in embodiments in which device 112 is an MR-LINAC, shield 106 may be a Faraday cage provided to prevent external radiofrequency signals from interfering with MR signals and affecting acquired images. According to some embodiments, in which treatment room wall 108 projects inwards into treatment room 102 to form housing 110, shield 106 may also project inwards into treatment room 102, thereby shielding components positioned within housing 110, such as device 112, from external radiofrequency signals. It will be appreciated that embodiments of the present disclosure may be utilized with systems configured differently than the configuration depicted in FIG. 1.

Housing 110 is situated within treatment room 102 and houses radiation therapy device 112. Device 112 is configured to at least partially surround a hollow bore 114 into which a patient may be placed, allowing for use of device 112 for applying therapeutic radiation to the patient and/or for acquiring images of the patient. Bore 114 may be cylindrical and may extend from the front face of housing 110 to the rear face of housing 110. Bore 114 is formed by an inner wall of housing 110 and may have a diameter large enough to accommodate both a patient and a patient support 116.

Support 116 is configured for supporting a patient in bore 114 of device 112. Support 116 is movable in a direction parallel to a horizontal axis of device 112, such that a patient resting on support 116 can be moved into and out of bore 114. Support 116 may form a cantilever section that projects away from a support structure 118. According to some embodiments, the patient may assume a supine position upon support 116. Support 116 may then be moved into bore 114 until the patient is correctly positioned for a radiation therapy process and, if desired, for a medical imaging process.

Shield 106 and treatment room wall 108 are at least partially surrounded by external wall 120, which may extend laterally beyond shield 106 to form machine room 104. A portion of shield 106 and a portion of treatment room wall 108 may form a barrier between treatment room 102 and machine room 104. Because housing 110 may be formed by an extension of shield 106 and treatment room wall 108 into treatment room 102, housing 110 may be an extension of machine room 104. Accordingly, components positioned within housing 110, such as radiation therapy device 112, are also positioned within machine room 104.

Bore 114 is configured to extend through radiation therapy device 112 from the front face of housing 110 to the back face of housing 110. The front and rear faces of housing 110 may be extensions of treatment room wall 108. Additionally, the front and rear openings of bore 114 are accessible only from treatment room 102, and the entire length of bore 114 is isolated from machine room 104 by the inner wall of housing 110.

Figure 2:
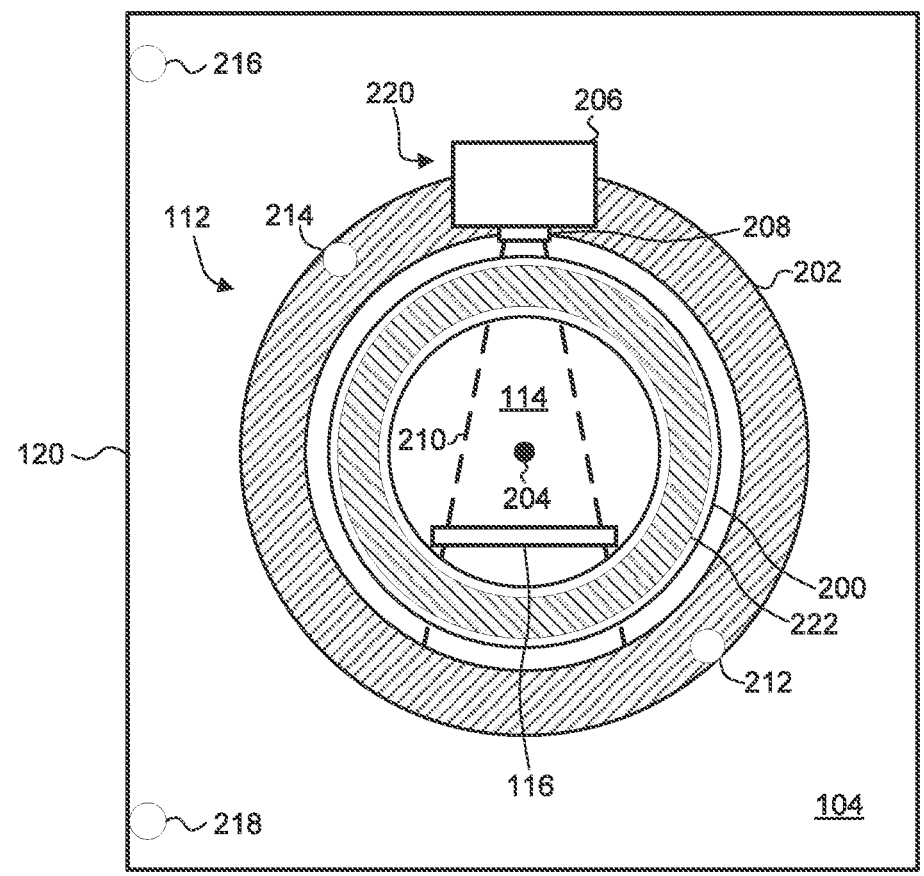
FIG. 2 illustrates an end view of an exemplary radiation therapy device positioned within the machine room of FIG. 1.

FIG. 2 illustrates an end view of an exemplary radiation therapy device positioned within machine room 104 of FIG. 1. Those skilled in the art will appreciate that certain features of device 112 have been omitted from the figure for clarity purposes.

Radiation therapy device 112 may include an MRI apparatus 200 for producing images of a patient positioned on support 116. MRI apparatus 200 includes one or more magnetic coils 222, each of which acts to generate a respective magnetic field for magnetic resonance imaging. One or more of magnetic coils 222 may have an axis that runs parallel to, or is coincident with, axis of rotation 204 (which is described in further detail below). Magnetic coils 222 may include one or more coils for generating a primary magnetic field, one or more coils for generating a gradient magnetic field, and/or one or more active shielding coils.

Bore 114 is formed by the interior space of MRI apparatus 200. Accordingly, bore 114 may be situated within one or more of magnetic coils 222. Additionally, in some embodiments, MRI apparatus 200 may be the inner-most component of radiation therapy device 112.

MRI apparatus 200 may additionally include an RF system which transmits radio signals towards the patient and detects the emitted signals at those frequencies so that the presence and location of protons in the patient can be determined. According to some embodiments, the RF system may include a single coil that both transmits the radio signals and receives the reflected emitted signals. According to some alternative embodiments, the RF system may include dedicated transmitting or receiving coils. According to yet further embodiments, the RF system may include multi-element phased array coils. The coil (or coils) of the RF system may form part of the magnetic coils 222.

Radiation therapy device 112 may additionally include a radiation therapy apparatus 220 which delivers a dose of radiation to a patient supported by support 116. Radiation therapy apparatus 220 may include a radiation source 206 and a beam shaping device 208 (collectively known as a radiation head), which together generate a beam of therapeutic radiation 210. Radiation source 206 may take any suitable form (e.g. a particle accelerator, such as a linear accelerator, or a radioactive material, such as cobalt-60, etc.). Beam shaping device 208 may be, for example, a multi-leaf collimator. Beam 210 may be formed using any suitable ionizing radiation, such as, for example, X-rays or gamma-rays. The radiation may have an energy level suitable for providing a therapy to a patient positioned on support 116. For example, a therapeutic X-ray beam may have an energy level greater than 1 MeV.

The radiation head is mounted on rotor 202 and is configured such that beam 210 is directed towards and intersects with axis 204. Although the present disclosure uses the term "rotor" to describe element 202, a person skilled in the art may also recognize element 202 as a "gantry". Rotor 202 is continuously rotatable, having an axis of rotation 204. Accordingly, radiation from the radiation head may be directed towards a patient on support 116 from multiple directions, reducing the dose which is delivered to healthy tissue surrounding the target for treatment (e.g. a tumor).

According to some embodiments, radiation therapy apparatus 220 of device 112 may lack the imaging panel of conventional linear accelerator systems. Instead, the imaging panel functionality is replaced by MRI apparatus 200.

The radiation head and rotor 202 are positioned radially outwards from MRI apparatus 200. Accordingly, radiation beam 210 may pass through a portion of MRI apparatus 200 before reaching a patient supported by support 116. According to some embodiments, magnetic coils 222 of MRI apparatus 200 include a window through which beam 210 may pass. According to some alternative embodiments, magnetic coils 222 may be thin enough that they are substantially transparent to beam 210. According to yet further embodiments, magnetic coils 222 may have a varying pitch, such that the pitch is relatively wide where the coils intersect beam 210, and relatively narrow in one or more regions outside beam 210.

MRI apparatus 200 can provide real-time imaging of a patient before, during, and/or after undergoing radiation therapy. During the course of radiation therapy, images of a target tissue and surrounding tissues may be acquired using MRI apparatus 200 to improve the placement accuracy of beam 210. For example, MRI apparatus 200 may be used to determine a location of a target organ or a target tumor in the patient, so as to accurately direct radiation therapy. Additionally, information collected by MRI apparatus 200 may be used to compensate for changes of the target tissue due to treatment or due to movement of the patient.

Rotor 202 carries radiation source 206 and beam shaping device 208, and is configured to rotate about MRI apparatus 200 during radiation therapy and/or during MRI imaging. Rotor 202 may be in the form of a drum and may be driven to rotate by a motor that engages with an edge of the drum. The motor may drive rotor 202 in a clockwise and/or a counterclockwise direction at a variety of speeds. Rotor 202 thus rotates about bore 114 and about axis of rotation 204. According to some embodiments, axis 204 is positioned at the center of bore 114 and/or at the center of rotor 202. Rotor 202 may also include a slip ring which at least partially surrounds rotor 202 and transmits power to it.

Rotor 202 additionally carries a first rotor-mounted antenna 212 and a second rotor-mounted antenna 214 (collectively hereafter, "rotor-mounted antennas"). In some embodiments, antennas 212 and 214 may be omnidirectional radio antennas and may be substantially equally spaced about axis of rotation 204. For example, antennas 212 and 214 may be angularly spaced 180° apart about rotor 202. Antennas 212 and 214 may be angularly positioned at any two opposite portions of rotor 202 so long as neither of antennas 212 and 214 is situated at the position of radiation source 206 and/or beam shaping device 208. Because antennas 212 and 214 are mounted upon rotor 202, they rotate in concert with the rotation of rotor 202. Antennas 212 and 214 may be positioned upon the same circumferential surface of rotor 202 and accordingly may be equidistant from the center of rotor 202, from the center of bore 114, and/or from axis 204.

According to some embodiments, antennas 212 and 214 are situated upon the outer-most circumferential surface of rotor 202. According to some alternative embodiments, antennas 212 and 214 are covered by an outer layer of rotor 202, such as a protective outer layer. However, according to these embodiments, the outer layer does not contain components of MRI apparatus 200 or components of the radiation head. Accordingly, signals emitted by and/or transmitted to antennas 212 and 214 are not attenuated by or otherwise affected by the outer layer.

External wall 120 extends along a side of machine room 104 and has a first stationary antenna 216 and a second stationary antenna 218 (collectively hereafter, "stationary antennas") mounted upon it. Antennas 216 and 218 may be omnidirectional radio antennas such that they may be configured to transmit radiofrequency signals and to receive radiofrequency signals. Antennas 216 and 218 may be configured for omnidirectional communication with antennas 212 and 214 such that antennas 216 and 218 may transmit signals to antennas 212 and 214, and vice versa. For example, antennas 216 and 218 may communicate with antennas 212 and 214 via radiofrequency signals. Antenna 216 may be positioned above axis of rotation 204. For example, antenna 216 may be positioned near the ceiling of machine room 104. Antenna 218 may be positioned below axis of rotation 204. For example, antenna 218 may be positioned near the floor of machine room 104.

Antennas 212-218 are positioned so as to allow line-of-sight radio communication between at least one of antennas 212 and 214 and at least one of antennas 216 and 218 at all angles of rotation of rotor 202. That is, the positioning of antennas 212-218 ensures that at all angles of rotation of rotor 202, at least one of antennas 212 and 214 is capable of transmitting radio signals to, and receiving radio signals from, at least one of antennas 216 and 218 without the radio signals being obstructed or impeded by components interposed between the antennas. Such unobstructed communication may be considered as line-of-sight communication, because the radio signal propagates along a straight path between the antennas. Hence, communication between the antennas 212, 214 and the antennas 216, 218 does not rely upon reflection or diffraction of radio signals. According to the exemplary rotor position depicted in FIG. 2, a direct line of unobstructed radio communication exists at least between rotor-mounted antenna 214 and stationary antenna 216. Each of rotor-mounted antennas 212 and 214 is configured for line-of-sight radio communication with each of stationary antennas 216 and 218, and vice versa.

Line-of-sight radio communication is possible at all angles of rotation of rotor 202 because, for every angle of rotation of rotor 202, at least one of the stationary antennas and at least one of the rotor-mounted antennas is arranged such that no portion of MRI apparatus 200, radiation source 206, or beam shaping device 208 obstructs, impedes or otherwise attenuates radio communication between the antennas. This is due, at least in part, to the fact that antennas 212 and 214 are positioned radially outwards from MRI apparatus 200, and are angularly spaced upon rotor 202 away from radiation source 206 and beam shaping device 208. This is also due, at least in part, to the relative orientations of the antennas 212-218. More particularly, because the antennas 212-218 are omnidirectional antennas, and because the antennas 212-218 are oriented parallel to each other (as described in more detail below), the direction of maximum gain of each rotor-mounted antenna 212, 214 coincides with the direction of maximum gain of each stationary antenna 216, 218 at all angles of rotation of the rotor 202.

According to some embodiments in which rotor-mounted antennas 212 and 214 are covered by a protective outer layer, line-of-sight radio communication is possible at all angles of rotation of rotor 202 because the protective outer layer does not contain any features or materials that attenuate or otherwise obstruct radio signals.

Figure 3:
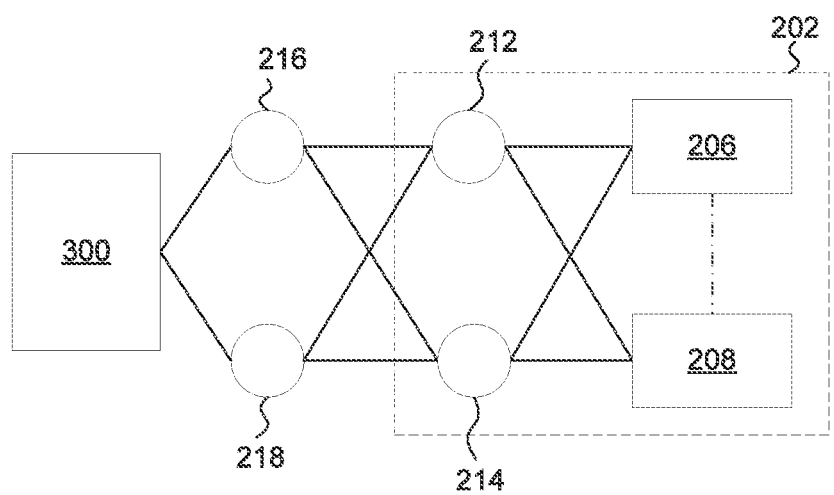
FIG. 3 illustrates an exemplary radiation therapy system and control unit.

FIG. 3 illustrates an exemplary radiation therapy system 100 and a system control unit 300. System 100 may additionally include system control unit 300, which is communicatively connected to and arranged to control various components of system 100, such as MRI apparatus 200, radiation source 206, beam shaping device 208, and the motor that drives rotation of rotor 202. In some embodiments, control unit 300 may be positioned outside of rooms 102 and 104. Control unit 300 is arranged to receive, store, and/or generate treatment plans for radiation source 206 and/or beam shaping device 208, such as selection and tracking of a target tissue or tumor, type of treatment, and treatment planning parameters (e.g., contours, dosages, beam angles, number of beams, etc.). According to some embodiments, control unit 300 may receive image data from MRI apparatus 200 and use the image data to guide generation and execution of treatment plans.

Control unit 300 is configured to communicate with rotor 202 and the components mounted thereon via antennas 212-218. Control unit 300 is communicatively coupled to stationary antennas 216 and 218 via one or both of a wired and a wireless connection. In use, control unit 300 may send signals to one or more of stationary antennas 216 and 218, which may transmit the signals to one or more of rotor-mounted antennas 212 and 214. Rotor-mounted antennas 212 and 214 may in turn relay the signals to components mounted on rotor 202, such as radiation source 206 and beam shaping device 208. Signals may also be generated by components mounted on rotor 202 and may be transmitted by one or more of antennas 212 and 214 to one or more of antennas 216 and 218. Antennas 216 and 218 may in turn relay the rotor-generated signals to control unit 300.

In some embodiments, stationary antennas 216 and 218 may be utilized to transmit control signals to rotor-mounted antennas 212 and 214. According to some embodiments, these control signals may originate from control unit 300. The control signals may include but are not limited to one or more of radiation therapy plans, radiation therapy parameters, and control signals to switch from a radiation therapy mode to an imaging mode, or vice versa. Because line-of-sight radio communication is possible at all angles of rotation of rotor 202, there are no periods of time during which communication between stationary antennas 216, 218 and rotor-mounted antennas 212, 214 is prevented by interposing components. In this manner, control signals can be transmitted to rotor 202 in real-time with no latency, allowing for real-time control of the components mounted on rotor 202 via the antennas.

Rotor-mounted antennas 212 and 214 may be utilized to transmit operational data and patient data to stationary antennas 216 and 218 and optionally to control unit 300 via antennas 216 and 218. Operational data may include, but is not limited to, one or more of feedback data pertaining to the operational mode of device 112 (e.g. if device 112 is operating in a radiation therapy mode or in a medical imaging mode, and the operational parameters of one or both modes), error data, and feedback data (e.g. data pertaining to rotor rotation direction and/or speed, and/or data pertaining to the radiation dose delivered to a patient). In some embodiments, rotor-mounted antennas 212 and 214 may transmit X-ray imaging data to stationary antennas 216 and 218. This X-ray data may be collected by a rotor-mounted X-ray imaging panel and may be used by the control unit 300 for calibration and quality assurance. For example, the X-ray imaging data may be used for quality control of collimator size and/or position. Patient data may include physical feedback data and/or image data collected from the patient during a radiation therapy procedure. As noted above, transmission of data between rotor-mounted antennas 212, 214 and stationary antennas 216, 218 is possible at all angles of rotation of rotor 202, with no periods of time during which communication is prevented by interposing components. As a result, a high frequency control loop may be established between control unit 300 and components mounted upon rotor 202, thereby allowing real-time control of a radiation therapy treatment session. The control loop may include one or more control signals being transmitted from the control unit 300 to components mounted on the rotor 202 (e.g. the radiation head), and one or more feedback signals being transmitted from components mounted on the rotor 202 to the control unit 300.

Because radiation therapy system 100 transmits signals onto and off rotor 202 via antennas 212-218 instead of via cables, such as those disclosed by the prior art, the rotation of rotor 202 is unrestricted. For example, rotor 202 may complete more than one full rotation in one direction without having to subsequently rotate in the opposite direction to unwind cables. The unrestricted rotation of rotor 202 provides greater freedom over how radiation is delivered to the patient. It also allows shorter procedure times than does the use of cables for communication because time need not be allocated for unwinding cables.

The arrangement of antennas 212-218 is additionally beneficial because it conforms with the spatial constraints of system 100. Because treatment room 102 and housing 110 are enclosed within shield 106, both are limited in space to minimize cost and to simplify installation. Machine room 104 is similarly limited in space to minimize the overall size of system 100. Additionally, the presence of bore 114 within rotor 202 limits the amount of space within rotor 202 that can accommodate antennas. However, stationary antennas 216 and 218 only require a small amount of space due to their limited number and small size, especially since they are spatially separated. Similarly, rotor-mounted antennas 212 and 214 are easily accommodated on rotor 202 due to their limited number, small size, and angular separation. Overall, the use of four antennas within system 100 may be optimal because it is the minimum number of antennas required to enable real-time control and communication onto and off rotor 202. Additionally, the presence of only four antennas takes up minimal space within system 100. While a four-antenna system is described as an example, it is contemplated that any suitable number of the antennas, such as five or more antennas, may also allow real-time control.

Figure 4:
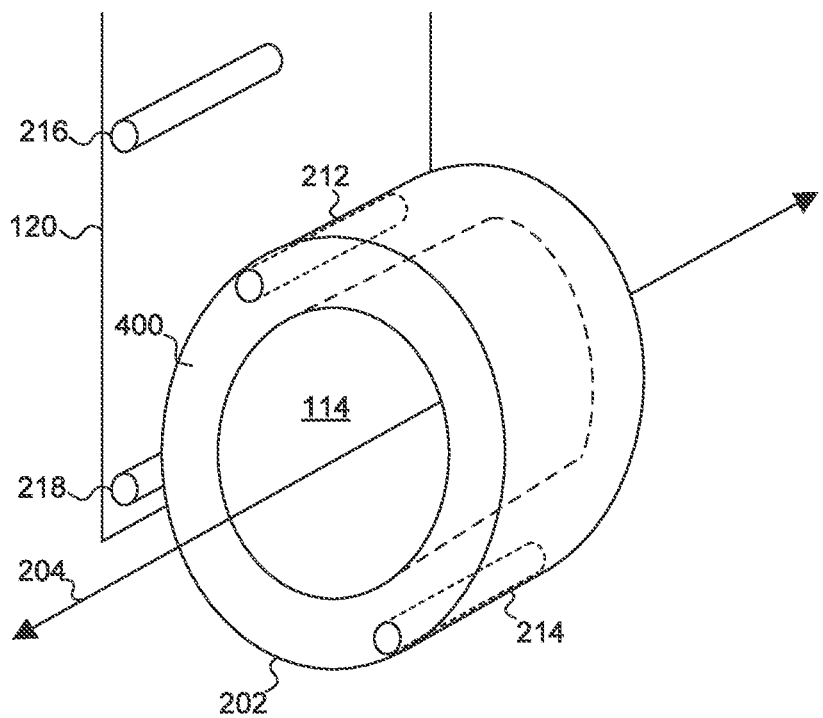
FIG. 4 illustrates an exemplary arrangement of the stationary antennas and the rotor-mounted antennas.

FIG. 4 illustrates an exemplary arrangement of stationary antennas 216 and 218 and rotor-mounted antennas 212 and 214. Antennas 212 and 214 are mounted upon a circumferential surface of rotor 202 such that they are mounted in a direction that is parallel to axis of rotation 204, which extends longitudinally along the centre of bore 114 and of rotor 202. Antennas 212 and 214 are mounted between a front face 400 of rotor 202 and a rear face (not shown) of rotor 202. In some embodiments, antennas 212 and 214 may extend along the entire longitudinal length of rotor 202. In some alternative embodiments, antennas 212 and 214 may extend along a fraction of the longitudinal length of rotor 202. In some embodiments, antennas 212 and 214 may have the same length and may be situated at the same longitudinal position along the length of rotor 202. In some embodiments, the front ends of antennas 212 and 214 may be positioned at or near front face 400 of rotor 202.

Stationary antennas 216 and 218 may have the same length as one or both of rotor-mounted antennas 212 and 214. Additionally, antennas 216 and 218 may be positioned at the same longitudinal position as antennas 212 and 214. Alternatively, one or more of antennas 216 and 218 may be positioned at a different longitudinal position than antennas 212 and 214.

Antennas 212-218 are omnidirectional and in some embodiments may be monopole antennas or dipole antennas. The utilization of monopole or dipole antennas may be beneficial because they do not require signal steering, as some more complex antennas do. Therefore, the monopole or dipole antennas may help ensure unobstructed, line-of-sight radio communication at all angles of rotation of rotor 202. In some embodiments, antennas 212-218 may be simple rod dipole antennas. The elements of antennas 212-218 are oriented in a direction that is parallel to axis 204.

Antennas 212-218 may be horizontally polarized and may have maximum gain in the horizontal direction.

To avoid multipath and destructive interference, system 100 may utilize one or more signal modulation schemes to provide signal redundancy. Generally speaking, the signal modulation schemes transmit multiple copies of the same data over the multiple communication channels that exist between the rotor-mounted antennas 212, 214 and the stationary antennas 216, 218. In this manner, reliable communication between the rotor-mounted antennas 212, 214 and the stationary antennas 216, 218 is possible at all angles of rotation of the rotor 202. In some embodiments, system 100 may utilize antenna diversity, wherein each of antennas 212-218 transmits a different signal. For example, space-time block coding (STBC) may be utilized, which provides very robust coding in terms of noise. This is beneficial for system 100 because the radiation therapy and/or medical imaging environment may produce occasional bursts of noise. STBC effectively compensates for channel problems, such as thermal noise and fading, and is additionally beneficial because it does not rely on polarization diversity. The use of the exemplary four antenna system, in combination with the STBC, eliminates any potential issues with local fading, cancellation, and blind spots. Alternatively, system 100 may utilize one or more other modulation schemes such as transmitting horizontal or vertical polarized copies of data, orthogonal frequency division multiplexing (OFDM), time diversity schemes, and coding diversity schemes.

In some embodiments, antennas 212-218 may transmit and receive radio signals in the GHz frequency band. For example, the signals may be in the ISM band (i.e. clustered around 2.4 GHz). Transmission of signals at this frequency allows antennas 212-218 to meet the large data requirements of system 100. For example, some radiation therapy systems have a 15-20 Mbit/second data requirement. Transmission in the ISM band, in combination with the unbroken radio communication between the stationary antennas and the rotor-mounted antennas, allows for the system to meet this big data requirement regardless of the rotational position of the rotor. However, one of skill in the art will understand that antennas 212-218 are capable of transmitting and receiving signals with data requirements far higher than 20 Mbit/second. Additionally, the GHz frequency band has a higher frequency than the critical frequency for magnetic resonance, which is in the MHz range. Therefore, communication amongst antennas 212-218 does not interfere with MR signals generated by MRI apparatus 200, and vice versa.

Figure 5:
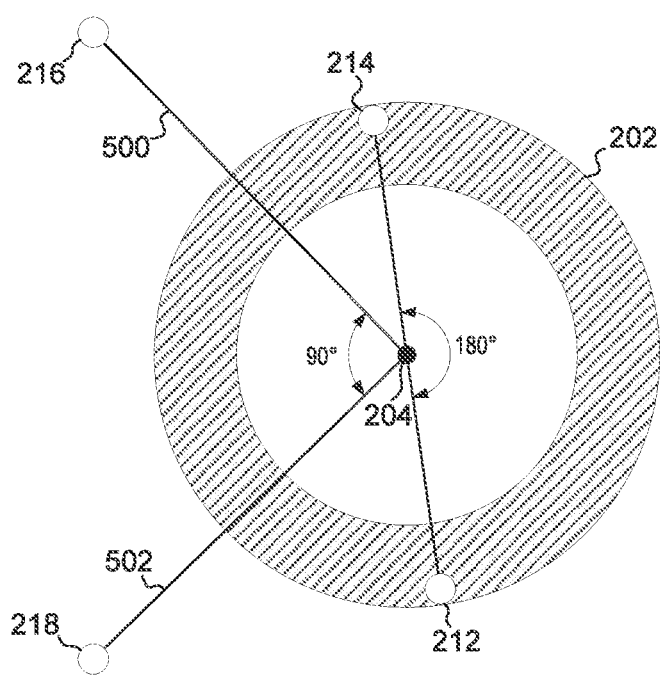
FIG. 5 illustrates exemplary relative positions of the stationary antennas and the rotor-mounted antennas.

FIG. 5 illustrates exemplary relative positions of stationary antennas 216 and 218 and rotor-mounted antennas 212 and 214. Rotor-mounted antennas 212 and 214 may be substantially equally spaced around axis of rotation 204 of rotor 202. For example, as depicted in FIG. 5, antennas 212 and 214 may be angularly spaced 180° apart about axis of rotation 204. This arrangement of rotor-mounted antennas 212 and 214 helps to ensure that at least one of antennas 212 and 214 has a line of unobstructed radio communication with at least one of stationary antennas 216 and 218 at all angles of rotation of rotor 202.

According to some embodiments, stationary antennas 216 and 218 may be positioned such that a straight line 500 between antenna 216 and axis 204 forms a right angle with a straight line 502 between antenna 218 and axis 204. This geometry of antennas 216 and 218 may be the optimal geometry for use with a two-antenna rotor because it may ensure that unobstructed line-of-sight radio communication exists for all angles of rotation of rotor 202. In some embodiments, the placement of antenna 216 above axis of rotation 204 and the placement of antenna 218 below axis of rotation 204 are additionally beneficial because they may allow for the right angle between line 500 and line 502.

Exemplary antenna systems of the present disclosure may provide a number of benefits. In some embodiments, the line-of-sight radio communication between rotor-mounted antennas 212 and 214 and stationary antennas 216 and 218 avoids communication blind spots and allows real-time communication between the rotor and the off-rotor control unit at all angles of rotation of rotor 202. This real-time communication may handle the large data requirements of radiation therapy systems and of combined radiation therapy and medical imaging systems. This real-time communication may also allow for real-time control loops between the control unit and rotor-mounted components. Additionally, the absence of cables allows the rotor to be freely rotated, without requiring unwinding of the cables between therapy sessions. This may reduce the overall time and cost of therapy. Further, the four antennas 212-218 require a small amount of space and may be easily incorporated within systems with limited space.

Although some exemplary embodiments of antenna system are disclosed above in connection with an MR-LINAC, it is contemplated that the disclosed antenna system may also be used within other therapy systems, such as a linear accelerator (LINAC) without an imaging component. The disclosed antenna system would obviate the need for a cable between a gantry, with radiation therapy components mounted thereon, and an off-gantry control system. This, in turn, would remove limitations on the rotation of the gantry, allowing greater freedom over how radiation is delivered to a patient with the radiation therapy components.

It is intended that the specification and examples be considered as exemplary only, with a true scope of the invention is indicated by the following claims and their equivalents.

The invention claimed is:

1. A radiation therapy apparatus comprising:
a rotor that is rotatable about an axis of rotation to a plurality of angles of rotation;
  a first plurality of omnidirectional radio antennas positioned on the rotor; and
  a second plurality of omnidirectional radio antennas configured to communicate with the first plurality of antennas, wherein each of the second plurality of antennas is positioned at a respective fixed location off the rotor so as to allow line-of-sight radio communication between at least one of the first plurality of antennas and at least one of the second plurality of antennas at each angle of rotation,
wherein the second plurality of antennas comprises a first antenna positioned above the axis of rotation and a second antenna positioned below the axis of rotation.

2. The apparatus in accordance with claim 1, wherein the first plurality of antennas are substantially equally spaced around the axis of rotation.

3. The apparatus in accordance with claim 1, wherein the first plurality of antennas and the second plurality of antennas include one of a monopole antenna and a dipole antenna.

4. The apparatus in accordance with claim 1, wherein each of the first plurality of antennas and each of the second plurality of antennas comprise an element that is oriented parallel to the axis of rotation.

5. The apparatus in accordance with claim 1, wherein the first plurality of antennas are positioned on a circumferential surface of the rotor, and wherein the circumferential surface of the rotor extends in a direction that is parallel to the axis of rotation.

6. The apparatus in accordance with claim 1, wherein each of the first plurality of antennas are positioned between a first face of the rotor and a second face of the rotor, and wherein a hollow bore extends between the first and second faces of the rotor.

7. The apparatus in accordance with claim 1, wherein the first plurality of antennas includes two antennas.

8. The apparatus in accordance with claim 1, wherein the second plurality of antennas are positioned such that the axis of rotation forms a right angle with the first antenna of the second plurality of antennas and the second antenna of the second plurality of antennas.

9. The apparatus in accordance with claim 1, wherein each of the first plurality of antennas and each of the second plurality of antennas transmit a different signal.

10. The apparatus in accordance with claim 1, wherein the apparatus utilizes one or more signal modulation schemes to provide redundant signals.

11. The apparatus in accordance with claim 1, wherein the radiation therapy apparatus is a linear accelerator.

12. The apparatus in accordance with claim 11, wherein the radiation therapy apparatus is a linear accelerator configured for use in combination with a medical imaging device.

13. The apparatus in accordance with claim 12, wherein the medical imaging device is a magnetic resonance imaging device.

14. The apparatus in accordance with claim 1, wherein the radiation therapy apparatus comprises a radiation source, the radiation source comprising a radioactive material.

15. The apparatus in accordance with claim 1, further comprising a radiation source and a radiation beam shaping device positioned on the rotor.

16. The apparatus in accordance with claim 15, wherein each of the first plurality of antennas is positioned angularly away from the radiation source and the radiation beam shaping device about the axis of rotation.

17. The apparatus in accordance with claim 1, further comprising an MRI apparatus positioned radially inward from the rotor.

18. The apparatus in accordance with claim 1, wherein the radio communication at each angle of rotation is in real time.

* * * * *